(12) United States Patent
Serafini et al.

(10) Patent No.: US 8,026,372 B2
(45) Date of Patent: Sep. 27, 2011

(54) PROCESS FOR THE PREPARATION OF ε-ALKOXYCARBONYLLYSINES AND THEIR ANALOGUES

(75) Inventors: Siro Serafini, Vicenza (IT); Riccardo Motterle, Vicenza (IT); Elena Brasola, Padova (IT)

(73) Assignee: F.I.S. Fabbrica Italiana Sintetici S.p.A., Vincenza (IT)

( * ) Notice: Subject to any disclaimer, the term of this patent is extended or adjusted under 35 U.S.C. 154(b) by 103 days.

(21) Appl. No.: 12/307,687

(22) PCT Filed: Aug. 4, 2006

(86) PCT No.: PCT/EP2006/007738
§ 371 (c)(1),
(2), (4) Date: Jan. 6, 2009

(87) PCT Pub. No.: WO2008/014811
PCT Pub. Date: Feb. 7, 2008

(65) Prior Publication Data
US 2009/0312557 A1 Dec. 17, 2009

(51) Int. Cl.
*C07D 249/00* (2006.01)
(52) U.S. Cl. .................. 548/255; 548/260; 548/533
(58) Field of Classification Search .................. 548/255, 548/260, 533
See application file for complete search history.

(56) References Cited

U.S. PATENT DOCUMENTS
4,942,248 A * 7/1990 Novy ............................ 548/533

OTHER PUBLICATIONS

Rzeszotarska et al., Darstellung von N-tert.-Alkyloxycarbonyl-aminosäuren mit Hilfe von tert.-Butyl- and tert.-Amyl-chinclyl-(8)-carbonat, Liebigs Annalen Der Chemie, vol. 716, pp. 216-218, 1968.
Katritzky, et al., "Synthesis of 1-(t-butoxycarbonyl)benzotriazole and 1-(p-Methoxybenzyloxycarbonyl)benzotriazole and Their Use in the Protection of Amino Acids" Synthetic Communications, vol. 27, No. 9,. 1623-1630, 1997.
Wünsch, "On the Synthesis of Benzyloxycarbonyl Amino Acids" Synthesis, pp. 958-960, Nov. 1986.
Rzeszotarska et al., Darstellung von N-tert.-Alkyloxycarbonyl-aminosäuren mit Hilfe von tert.-Butyl- und tert.-Amyl-chinolyl-(8)-carbonat, Liebigs Annalen Der Chemie, vol. 716, pp. 216-218, 1968.

* cited by examiner

*Primary Examiner* — Susannah Chung
(74) *Attorney, Agent, or Firm* — Dickstein Shapiro LLP

(57) ABSTRACT

A process for the preparation of ω-alkoxycarbonylamino-α-aminoacids and α,ω orthogonally diprotected diaminoacids from α,ω-diaminoacids using 1-alkoxycarbonylbenzotriazoles as protecting agents is disclosed. In an alternative embodiment, carbamoylating agents in the presence of benzotriazoles are used instead of 1-alkoxycarbonylbenzotriazoles. This reaction is preferably applied to the preparation of ε-alkoxycarbonyllysines from lysine. A process for the preparation of t-butoxycarbonylbenzotriazoles and novel complexes of ω-alkoxycarbonylamino-α-aminoacids with benzotriazoles are also disclosed.

28 Claims, No Drawings

PROCESS FOR THE PREPARATION OF ε-ALKOXYCARBONYLLYSINES AND THEIR ANALOGUES

TECHNICAL FIELD OF THE INVENTION

The present invention is directed to a process for the preparation of ω-alkoxycarbonylamino-α-aminoacids from α,ω-diaminoacids and, preferably, of ε-alkoxycarbonyllysines from lysine.

BACKGROUND ART

It is well known in the aminoacids and peptides chemistry that it is essential to regioselectively protect the terminal amino group (in ω) of the side chain of lysine and its analogues. This allows reacting selectively the α amino group and, in case, orthogonally protecting the α and ω amino groups. The possibility of selectively introducing two protecting orthogonal groups into an α,ω-diaminoacid increases its potential uses in general chemistry and particularly in pharmaceutical chemistry. The alkoxycarbonyl groups (or carbamates) are the most versatiles and widely used protecting groups for aminoacids.

Because of the synthetic importance of the protection of α,ω-diaminoacids in the ω position, several studies have been dedicated to this subject. The classical method, still widely applied, involves the formation of a copper II complex to block the α nitrogen and to selectively protect the ω position (*J. Biol. Chem.* (1941), 140, 705-10). This methodology is long and tedious since it requires several reactions: first the formation of the copper complex, then the α protection and eventually the liberation of the complex with EDTA or hydrogen sulfide. Due to its toxicity, residuals of copper must not pollute the protected aminoacid and this requires a further purification procedure (*Tetrahedron Lett.* (2004), 45(50), 9297-9298). Moreover the maximum concentration of copper in wastewaters is set by the Italian law at 0.1 ppm; in addition to the cost of the metal itself, also the cost of disposal and decontamination of the mother liquors must thus be taken into account. In conclusion this methodology is suitable for small preparations on a laboratory scale, but not for industrial productions.

Chemists have tried over time several alternatives, among them the use of special reagents such as, in the case of an introduction of a BOC group in the ε position of a lysine, Boc-hydroxyquinoline (*Liebigs Ann. Chem.* (1968), 716, 216-18) and 2-(Boc-oxyimino)-2-phenylacetonitrile (*Org. Prep. Proced. Int.* (1983), 15(6), 379-85). However all these reagents either give low yields or are expensive, making them unsuitable for large scale application.

Finally some benzotriazole carbamates, such as Boc-benzotriazole (U.S. Pat. No. 4,942,248; *Synth. Commun.* (1997), 27(9), 1623-1630) and Z-benzotriazole (*Synthesis* (1986), (11), 958-60) have been used to protect aminoacids, but never for α,ω-diaminoacids, nor any regioselectivity of their reactions has been reported.

From the drawbacks of the known processes it is clear that there is still the need for a process for the preparation of ω-alkoxycarbonylamino-α-aminoacids and of α,ω orthogonally diprotected diaminoacids from α,ω-diaminoacids which is applicable on an industrial scale with high yields and uses cheap and non-polluting reagents.

BRIEF DESCRIPTION OF THE INVENTION

We have surprisingly found a process for the preparation of ω-alkoxycarbonylamino-α-aminoacids and α,ω orthogonally diprotected diaminoacids from α,ω-diaminoacids using 1-alkoxycarbonylbenzotriazoles as protecting agents. In an alternative embodiment, carbamoylating agents in the presence of benzotriazoles are used instead of 1-alkoxycarbonylbenzotriazoles. This reaction is preferably applied to the preparation of ε-alkoxycarbonyllysines from lysine. A process for the preparation of t-butoxycarbonylbenzotriazoles and novel complexes of ω-alkoxycarbonylamino-α-aminoacids with benzotriazoles are also provided.

DETAILED DESCRIPTION OF THE INVENTION

A process is provided for the preparation of an ω-alkoxycarbonylamino-α-aminoacid of formula 1

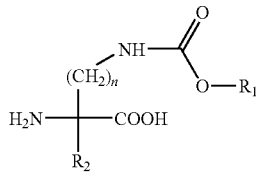

wherein n is a number from 2 to 6, $R_1$ is $C_1$-$C_{12}$ alkyl, $C_1$-$C_{12}$ cycloalkyl or $C_1$-$C_6$ alkenyl, all optionally substituted with aryl, heteroaryl, halogen, $C_1$-$C_4$ alkylthio, $C_1$-$C_4$ alkylsulphonyl, arylsulphonyl, or trimethylsilyl, wherein aryl and heteroaryl may be substituted or unsubstituted, $R_2$ is hydrogen or methyl, optionally substituted with halogen atoms, comprising reacting an α,ω-diaminoacid of formula 2

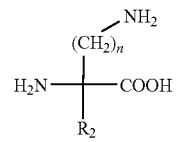

wherein n and $R_2$ have the same meaning as above,
with a 1-alkoxycarbonylbenzotriazole of formula 3

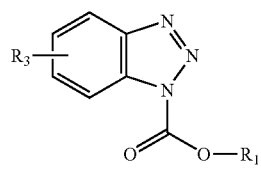

wherein $R_1$ has the same meaning as above and $R_3$ means from 0 to 2 substituents chosen from the group consisting of methyl, trifluoromethyl, chlorine, bromine and nitro.

An alternative process is provided for the preparation of an ω-alkoxycarbonylamino-α-aminoacid of formula 1

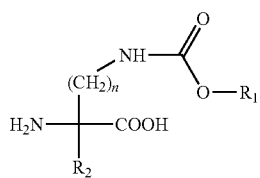

wherein n, $R_1$ and $R_2$ have the same meaning as above, comprising reacting an α,ω-diaminoacid of formula 2

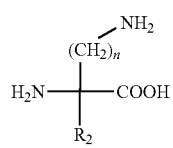

wherein n and $R_2$ have the same meaning as above, with a benzotriazole of formula 4

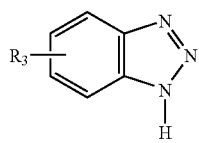

wherein $R_3$ has the same meaning as above, and a carbamoylating agent of formula 5

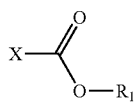

wherein $R_1$ has the same meaning as above and X is an activating group for the carboxylic group.

Preferred compounds of formula 1 are compounds of formula 1a, i.e. belonging to the L steric series, which may be prepared from the corresponding compounds of formula 2a.

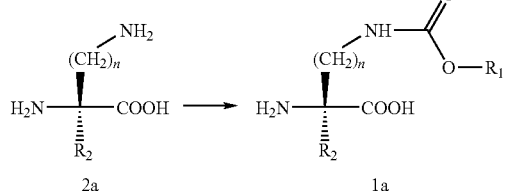

n is preferably 3 or 4, more preferably n is 4;
$R_1$ is preferably chosen from the group consisting of t-butyl, benzyl, methyl, ethyl, allyl, 2,4-dichlorobenzyl, 2-(biphenylyl)isopropyl, 9-fluorenylmethyl, more preferably is t-butyl or benzyl;
$R_2$ is preferably hydrogen, methyl, or difluoromethyl, more preferably is hydrogen;
$R_3$ is preferably not present;

X is preferably halogen, azide, aryloxy or a group $OCOOR_1$, wherein $R_1$ has the same meaning as above, more preferably X is chlorine, phenoxy or a group $OCOOR_1$.

Particularly preferred α,ω-diaminoacids of formula 2 are L-lysine and L-ornithine, even more particularly preferred is L-lysine. Other examples of α,ω-diaminoacids of formula 2 are synthetic aminoacids such as 2,4-diaminobutanoic acid, 2,7-diaminoheptanoic acid, 2,8-diaminooctanoic acid and α-(difluoromethyl)ornithine.

Particularly preferred carbamoylating agents of formula 5 are chosen from the group consisting of benzyl chloroformate, di-t-butyl dicarbonate ((Boc)$_2$O) and t-butyl phenyl carbonate.

Particularly preferred ω-alkoxycarbonylamino-α-aminoacids of formula 1 are chosen from the group consisting of ε-t-butoxycarbonyl-L-lysine (H-Lys(Boc)-OH) and ε-benzyloxycarbonyl-L-lysine (H-Lys(Z)-OH).

The following reaction schemes show the general reactions and particularly preferred embodiments of the invention.

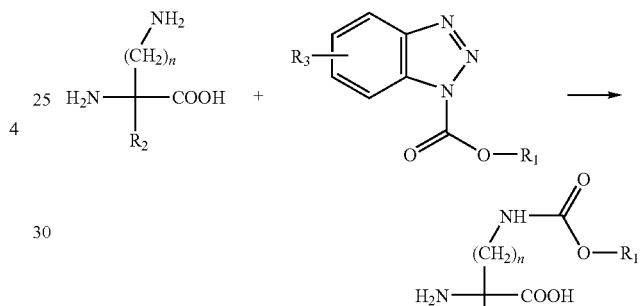

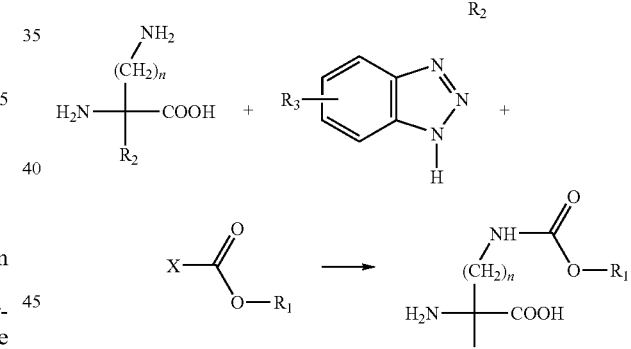

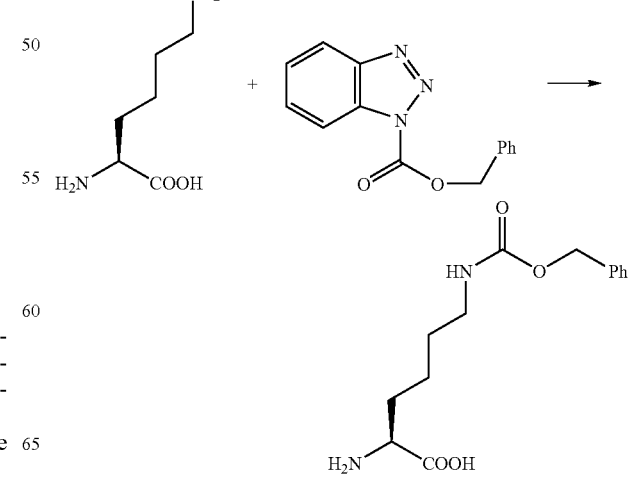

-continued

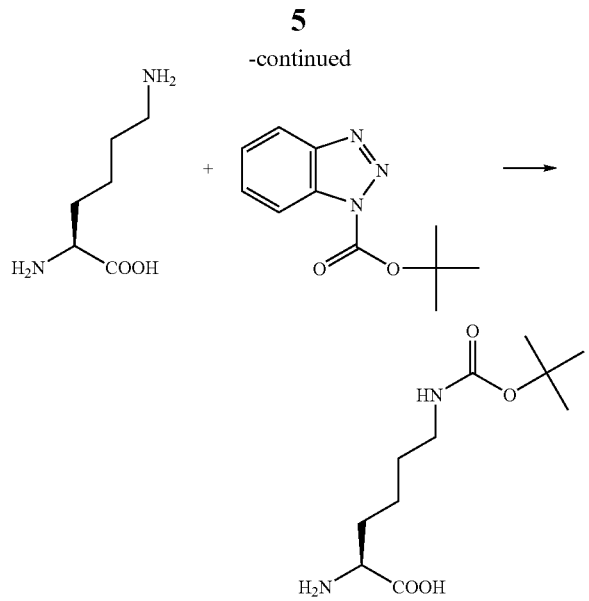

1-Alkoxycarbonylbenzotriazoles of formula 3 may be prepared by reaction of benzotriazoles of formula 4 with carbamoylating agents of formula 5. The reaction is preferably carried out in THF or dioxane at a temperature from 10 to 30° C. Depending on the choice of the carbamoylating agent, a base is preferably used to capture the acid that may evolve. 4-Dimethylaminopyridine is preferably used as catalyst. The reaction is usually complete in a few hours.

In the known art (U.S. Pat. No. 4,942,248; *Synth. Commun.* (1997), 27(9), 1623-1630), t-butoxycarbonylbenzotriazole is prepared by reaction of benzotriazole with phosgene and subsequent reaction with t-butanol; the drawback of the known process is the use of phosgene, which is a very toxic gas requiring special handling procedures. In a further aspect of the present invention a process is provided for the preparation of a t-butoxycarbonylbenzotriazole of formula 6

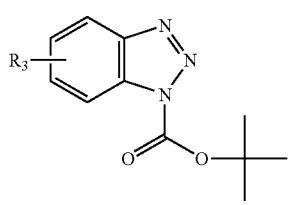

6 wherein $R_3$ has the same meaning as above, comprising reacting a benzotriazole of formula 4

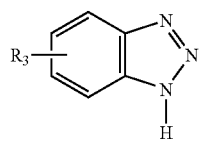

4 wherein $R_3$ has the same meaning as above, with $(Boc)_2O$. This avoids the use of phosgene and proceeds under mild reaction conditions.

The reaction of an α,ω-diaminoacid of formula 2 with a 1-alkoxycarbonylbenzotriazole of formula 3 is preferably carried out at a pH equal to or greater than 11, in order to deprotonate the ω-amino group, which is the most basic amino group in the molecule. Preferred solvents are mixtures of water and THF or water and dioxane. The carbamoylation reaction is usually completed in a few hours at 0° C. The resulting ω-alkoxycarbonylamino-α-aminoacid may be purified with standard methods, such as crystallization or ion exchange chromatography, or salt formation with dicyclohexylamine, or immediately reacted with another carbamoylating agent to provide orthogonally diprotected α,ω-diaminoacids.

As already mentioned, in an alternative aspect of the present invention an α,ω-diaminoacid of formula 2 is reacted with a benzotriazole of formula 4 and a carbamoylating agent of formula 5. The selectivity of this method may be due to the formation in situ of 1-alkoxycarbonylbenzotriazoles of formula 3 that subsequently react selectively with α,ω-diaminoacids. The reaction is preferably carried out in the same reaction conditions of the reaction of α,ω-diaminoacids with 1-alkoxycarbonylbenzotriazoles.

In a further aspect of the present invention we have provided novel complexes of formula 7 of an ω-alkoxycarbonylamino-α-aminoacid with a benzotriazole of formula 4. The ratio between the protected aminoacid and the benzotriazole is 2:1.

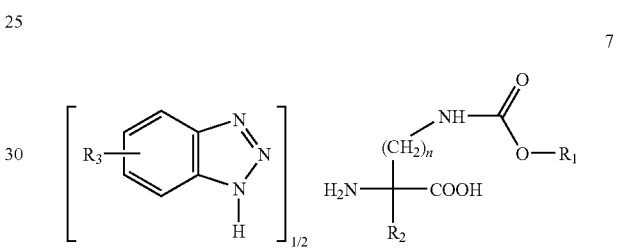

7 wherein n, $R_1$, $R_2$ and $R_3$ have the same meaning as above.

In formula 7, $R_1$ is preferably t-butyl.

As already mentioned, ω-alkoxycarbonylamino-α-aminoacid of formula 1 are also useful intermediates in the preparation of α,ω orthogonally diprotected diaminoacids. In a further aspect of the present invention a process is thus provided for the preparation of α,ω orthogonally diprotected diaminoacids of formula 8

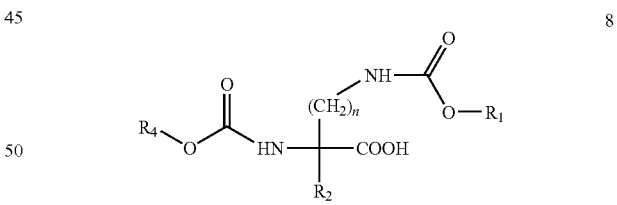

8 wherein n, $R_1$ and $R_2$ have the same meaning as above and $R_4$ is $C_1$-$C_{12}$ alkyl, $C_1$-$C_{12}$ cycloalkyl or $C_1$-$C_6$ alkenyl, all optionally substituted with aryl, heteroaryl, halogen, $C_1$-$C_4$ alkylthio, $C_1$-$C_4$ alkylsulphonyl, arylsulphonyl, or trimethylsilyl, wherein aryl and heteroaryl may be substituted or unsubstituted and $R_4$ is different from $R_1$, comprising the steps of (a) preparing an ω-alkoxycarbonylamino-α-aminoacids of formula 1 according to the method previously disclosed,
(b) protecting the α-amino group.

$R_4$ is preferably chosen from the group consisting of t-butyl, benzyl, methyl, ethyl, allyl, 2,4-dichlorobenzyl, 2-(biphenylyl)isopropyl, 9-fluorenylmethyl, more preferably is t-butyl or benzyl.

The protection of the α-amino group may be performed as well known in the art (Greene, Theodora W.; Wuts, Peter G. M. *Protective Groups in Organic Synthesis*, 3$^{rd}$ ed. (1999), John Wiley & sons Inc., 503-550), also using Schotten-Baumann conditions. The intermediate ω-alkoxycarbonylamino-α-aminoacid of formula 1 may be isolated and purified before the introduction of the second protecting group; preferably the second protecting group is introduced without the isolation of the monoprotected derivative.

α,ω Orthogonally diprotected diaminoacids of formula 8 may be purified by salt formation with a base, preferably with dicyclohexylamine.

We have thus provided a process for the preparation of ω-alkoxycarbonylamino-α-aminoacids that allows a simple, but selective protection of the ω-amino group of α,ω-diaminoacids, which is environmentally friendly (it does not make use of toxic reagents like copper salts), proceeds with good yield and selectivity and is well suited for industrial application.

The following examples are set forth to aid in understanding the invention, but are not intended to limit the scope of protection.

EXAMPLES

Example 1

H-Lys(Boc)-OH

A solution of di-t-butyl dicarbonate (13.6 g, 62.3 mmol) in THF (31 mL) was treated with benzotriazole (8.0 g, 67.2 mmol) and dimethylaminopyridine (25 mg, 0.21 mmol). After 3 hours the mixture was slowly poured, stirring at 0° C. and maintaining pH 12 with aqueous sodium hydroxide, into a solution of L-lysine (10.0 g, 68.4 mmol) in water (80 mL) at pH 12. After further 2 hours most of the THF was removed at reduced pressure. The remaining water solution was extracted 3 times with ethyl acetate to recover 46% of the initial benzotriazole. The solution was then treated with hydrochloric acid to pH 5.6, obtaining the precipitation of a solid, which was stirred overnight and filtered. The product (17.7 g, 93%) is the complex 1/2 benzotriazole with H-Lys(Boc)-OH ($^1$H-NMR, $^{13}$C-NMR, LC-MS), which can be used directly or purified by sublimation (140° C., 0.3 mbar, 3 hours) to remove the benzotriazole (quantitative). The product contains 7% lysine and 4% Boc-Lys-OH.

A further purification is possible by ion exchange column chromatography (citrate or phosphate buffer, pH 5, sulfonic resin DOWEX 50 WX2, 50-100 mesh). The recovered product is H-Lys(Boc)-OH essentially free from impurities ($^1$H-NMR, $^{13}$C-NMR, LC-MS, purification yield 81%).

Example 2 (Comparative)

H-Lys(Boc)-OH

Example 1 was repeated without benzotriazole. A product mixture was obtained: 43.5% H-Lys(Boc)-OH and 56.5% Boc-Lys-OH (LC-MS).

Example 3

H-Orn(Boc)-OH

A solution of di-t-butyl dicarbonate (2.36 g, 10.8 mmol) in THF (10 mL) was treated with benzotriazole (1.42 g, 11.9 mmol) and dimethylaminopyridine (4 mg, 0.03 mmol). After 1 hour the mixture was slowly poured, stirring at 0° C. and maintaining pH 12 with aqueous sodium hydroxide, into a solution of L-ornithine hydrochloride (2.0 g, 11.9 mmol) in water (10 mL) at pH 12. After further 2 hours THF was removed at reduced pressure. The remaining water solution was extracted 3 times with ethyl acetate to recover 48% of the initial benzotriazole. The solution was then treated with hydrochloric acid to pH 5.6, obtaining the precipitation of a solid, which was stirred overnight and filtered. The product (2.63 g, 83%) is the complex 1/2 benzotriazole with H-Orn(Boc)-OH ($^1$H-NMR, $^{13}$C-NMR, LC-MS), which can be used directly or purified. The product contains approximately 7% ornithine and 4% Boc-Orn-OH.

Example 4

H-Lys(Boc)-OH

A solution of di-t-butyl dicarbonate (6.0 g, 27.5 mmol) in THF (10 mL) was slowly added, stirring at 0° C. and maintaining pH 12 with aqueous sodium hydroxide, into a solution of L-lysine (4.0 g, 27.4 mmol) and benzotriazole (3.3 g, 27.7 mmol) in water (10 mL) and THF (11 mL) at pH 12. After 16 hours most of the THF was removed at reduced pressure and the remaining water solution was extracted 3 times with ethyl acetate. The solution was then treated with hydrochloric acid to pH 5.6, stirred overnight and filtered. The product (7.7 g, 92%) is the complex 1/2 benzotriazole with H-Lys(Boc)-OH ($^1$H-NMR, $^{13}$C-NMR, LC-MS).

Example 5

H-Lys(Boc)-OH

A solution of L-lysine monohydrochloride (20.0 g, 109.5 mmol) and benzotriazole (14.3 g, 120.0 mmol) in a mixture of water (66.6 mL) and THF (111.0 mL) at pH 12 was treated with t-butyl phenyl carbonate (24.3 mL, 131.4 mmol) and stirred 18 hours at 60° C. The mixture, initially 2 layers, became a clear orange solution and the product was approximately 75% (NMR).

Example 6

H-Lys(Z)-OH

A solution of benzyl chloroformate (7.3 mL, 51.9 mmol) in THF (70 mL) was treated with benzotriazole (6.1 g, 51.2 mmol) and dimethylaminopyridine (83 mg, 0.68 mmol). The mixture was stirred at room temperature for 4 hours, while maintaining pH 10 with aqueous sodium hydroxide, and a thin suspension was obtained. This mixture was slowly poured, stirring at 0° C. and maintaining pH 12 with aqueous sodium hydroxide, into a solution of L-lysine (5.0 g, 34.2 mmol) in water (75 mL) at pH 12. After adding further 50 mL of THF and 50 mL of water, the reaction mixture was stirred overnight, then partly concentrated under vacuum and treated with hydrochloric acid to pH 5.6. The suspension was filtered and the residue washed 3 times with chloroform. The product (7.3 g, 76%) is the expected H-Lys(Z)-OH ($^1$H-NMR, $^{13}$C-NMR, ESI-MS).

Example 7

H-Lys(Z)-OH

A solution of benzyl chloroformate (1.84 g, 10.8 mmol) in THF (5 mL) was slowly added, stirring at 0° C. and maintaining pH 12 with aqueous sodium hydroxide, into a solution of L-lysine (1.7 g, 11.6 mmol) and benzotriazole (1.42 g, 11.9 mmol) in water (7 mL) and THF (11 mL) at pH 12, obtaining a suspension. After adding a further 25 mL of THF and 25 mL of water to obtain a clear solution, the reaction mixture was stirred overnight, concentrated under vacuum, extracted with ethyl acetate, treated with hydrochloric acid to pH 6 and filtered. The product (1.64 g, 54%) is the expected H-Lys(Z)-OH ($^1$H-NMR, $^{13}$C-NMR, ESI-MS).

Example 8

Z-Lys(Boc)-OH Dicyclohexylamine Salt

A solution of di-t-butyl dicarbonate (26.0 g, 119 mmol) in THF (52 mL) was treated with benzotriazole (16 g, 134 mmol) and dimethylaminopyridine (50 mg, 0.41 mmol). After 2 hours the mixture was slowly poured, stirring at 0° C. and maintaining pH 11.5 with aqueous sodium hydroxide, into a solution of L-lysine monohydrochloride (20.0 g, 109.5 mmol) in water (60 mL) at pH 11.5. After stirring overnight, benzyl chloroformate (16 mL, 114 mmol) was slowly added at 0° C.: the pH decreased from 11 to 10. After 2 hours the solvent was removed under vacuum and the residue was taken up with 200 mL of isopropyl acetate and 200 mL of water. At 0° C. the pH was lowered to 2 with concentrated hydrochloric acid. The aqueous layer was discarded and the organic layer was washed with 100 mL of water. After anhydrification with sodium sulfate, the clear solution was treated with dicyclohexylamine (40 mL, 201 mmol) and stirred overnight. The suspension was filtered, washed with isopropyl acetate and dried giving 39.4 g (64%) of product, 38.5 g of which were recrystallized from 308 mL of methyl ethyl ketone to give a first crop of 36 g of Z-Lys(Boc)-OH dicyclohexylamine salt after drying (60%; purity 94.5%, $^1$H-NMR, HPLC).

The invention claimed is:

1. Process for the preparation of an ω-alkoxycarbonylamino-α-aminoacid of formula 1

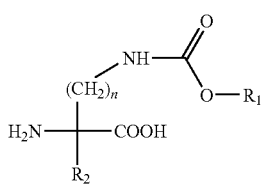

wherein n is a number from 2 to 6, $R_1$ is $C_1$-$C_{12}$ alkyl, $C_1$-$C_{12}$ cycloalkyl or $C_1$-$C_6$ alkenyl, all optionally substituted with aryl, heteroaryl, halogen, $C_1$-$C_4$ alkylthio, $C_1$-$C_4$ alkylsulphonyl, arylsulphonyl, or trimethylsilyl, wherein aryl and heteroaryl may be substituted or unsubstituted, $R_2$ is hydrogen or methyl, optionally substituted with halogen atoms, comprising reacting in a solvent an α,ω-diaminoacid of formula 2

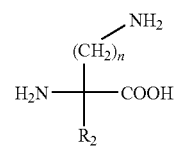

wherein n and $R_2$ have the same meaning as above, with a 1-alkoxycarbonylbenzotriazole of formula 3

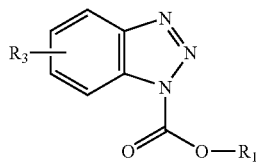

wherein $R_1$ has the same meaning as above and $R_3$ means from 0 to 2 substituents chosen from the group consisting of methyl, trifluoromethyl, chlorine, bromine and nitro.

2. The process according to claim 1 wherein the said step of reacting an α,ω-diaminoacid of formula 2 comprises reacting in situ a benzotriazole of formula 4

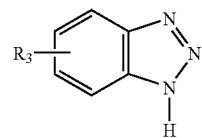

wherein $R_3$ has the same meaning as in claim 1, with a carbamoylating agent of formula 5

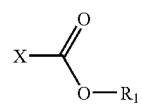

wherein $R_1$ has the same meaning as in claim 1 and X is an activating group for the carboxylic group.

3. The process according to claim 1 wherein said 1-alkoxycarbonylbenzotriazole of formula 3 is preformed and added to said α,ω-diaminoacid of formula 2.

4. The process according to claim 3 wherein said 1-alkoxycarbonylbenzotriazole of formula 3 is preformed by reacting a benzotriazole of formula 4 with a carbamoylating agent of formula 5.

5. The process according to claim 1 wherein compounds of formula 1 belong to the L steric series.

6. The process according to claim 1 wherein n is 3 or 4.

7. The process according to claim 1 wherein n is 4.

8. The process according to claim 1 wherein $R_1$ is chosen from the group consisting of t-butyl, benzyl, methyl, ethyl, allyl, 2,4-dichlorobenzyl, 2-(biphenylyl)isopropyl, 9-fluorenylmethyl.

9. The process according to claim 1 wherein $R_1$ is t-butyl or benzyl.

10. The process according to claim 1 wherein $R_2$ is hydrogen, methyl, or difluoromethyl.

11. The process according to claim 1 wherein $R_2$ is hydrogen.

12. The process according to claim 1 wherein $R_3$ is not present.

13. The process according to claim 2 wherein X is halogen, azide, aryloxy or a group $OCOOR_1$.

14. The process according to claim 2 wherein X is chlorine, phenoxy or a group $OCOOR_1$.

15. The process according to claim 1 wherein the α,ω-diaminoacid of formula 2 is L-lysine or L-ornithine.

16. The process according to claim 1 wherein the α,ω-diaminoacid of formula 2 is L-lysine.

17. The process according to claim 2 wherein the carbamoylating agents of formula 5 is chosen from the group consisting of benzyl chloroformate, di-t-butyl dicarbonate and t-butyl phenyl carbonate.

18. The process according to claim 1 wherein the ω-alkoxycarbonylamino-α-aminoacid of formula 1 is chosen from the group consisting of ε-t-butoxycarbonyl-L-lysine and ε-benzyloxycarbonyl-L-lysine.

19. The process according to claim 1 which is carried out in THF or dioxane.

20. The process according to claim 1 which is carried out at a pH equal to or greater than 11.

21. The process according to claim 2, further comprising an intermediate comprising a complex of formula 7 of an ω-alkoxycarbonylamino-α-aminoacid with a benzotriazole of formula 4

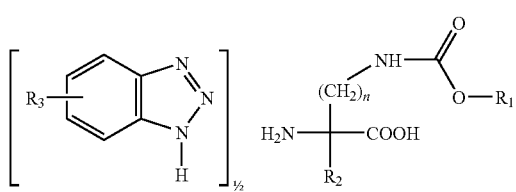

7 wherein n, $R_1$, $R_2$ and $R_3$ have the same meaning as in claim 1.

22. A complex of formula (7)

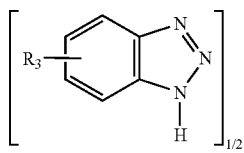

7

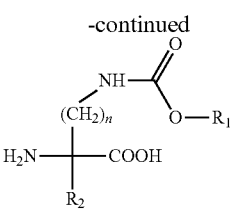

wherein n is a number from 2 to 6, $R_1$ is t-butyl, $R_2$ is hydrogen or methyl, optionally substituted with halogen atoms, and $R_3$ means from 0 to 2 substituents chosen from the group consisting of methyl, trifluoromethyl, chlorine, bromine and nitro.

23. The process according to claim 1, further comprising a process for the preparation of α,ω orthogonally diprotected diaminoacids of formula 8

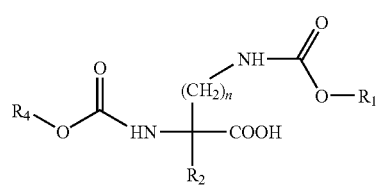

8 wherein n, $R_1$ and $R_2$ have the same meaning as in claim 1 and $R_4$ is $C_1$-$C_{12}$ alkyl, $C_1$-$C_{12}$ cycloalkyl or $C_1$-$C_6$ alkenyl, all optionally substituted with aryl, heteroaryl, halogen, $C_1$-$C_4$ alkylthio, $C_1$-$C_4$ alkylsulphonyl, arylsulphonyl, or trimethylsilyl, wherein aryl and heteroaryl may be substituted or unsubstituted and $R_4$ is different from $R_1$, comprising the steps of:
(a) preparing an ω-alkoxycarbonylamino-α-aminoacids of formula 1 according to claim 1,
(b) protecting the α-amino group.

24. The process according to claim 23 wherein $R_4$ is chosen from the group consisting of t-butyl, benzyl, methyl, ethyl, allyl, 2,4-dichlorobenzyl, 2-(biphenylyl)isopropyl, 9-fluorenylmethyl.

25. The process according to claim 23 wherein $R_4$ is chosen from the group consisting of t-butyl or benzyl.

26. The process according to claim 23 wherein the second protecting group is introduced without the isolation of the monoprotected derivative.

27. The process according to claim 23 wherein the α, ω orthogonally diprotected diaminoacid is purified by salt formation with a base.

28. The process according to claim 23 wherein the α, ω orthogonally diprotected diaminoacid is purified by salt formation with dicyclohexylamine.

* * * * *